United States Patent [19]

Lonca

[11] Patent Number: 4,722,688
[45] Date of Patent: Feb. 2, 1988

[54] DENTAL IMPLANTS AND ACCESSORIES THEREFOR

[76] Inventor: Philippe Lonca, Centre Commercial LE BARP, 33830 Belin, France

[21] Appl. No.: 841,184

[22] Filed: Mar. 19, 1986

Related U.S. Application Data

[63] Continuation of Ser. No. 416,675, Sep. 25, 1982, abandoned.

[30] Foreign Application Priority Data

Sep. 16, 1981 [FR] France ................................. 81 17607

[51] Int. Cl.[4] ................................................. A61C 8/00
[52] U.S. Cl. .................................. 433/173; 433/201.1
[58] Field of Search ................ 433/173, 174, 175, 201

[56] References Cited

U.S. PATENT DOCUMENTS 3,557,454  1/1971  Whitehill et al. ..................... 433/220
3,717,932  2/1973  Brainin ................................. 433/175
4,195,409  1/1980  Child ................................... 433/175

Primary Examiner—Robert Peshock
Attorney, Agent, or Firm—Robert J. Koch

[57] ABSTRACT

An implant of one-piece construction is made of a carbon carbon composite material having a texture of carbon fibers and a fiber interconnecting matrix also of carbon. The implant comprises a root portion and a coronal portion which may be frustoconical or cylindrical. A peripheral groove may be formed between the root and coronal portions permitting gum growth to grip the implant. The implant may be finned. A plurality of implants may be provided on a perforate blade. The axis of the coronal portion may be inclined relative to the axis of the root portion. In an embodiment, the root portion is gable roof-shaped and may be joined by a rod to form twin implants. Accessories adapted to the implant for mounting the dental crown are also shwon as well as a surgical instrument for cutting the gums before drilling the socket in the jawbone.

6 Claims, 23 Drawing Figures

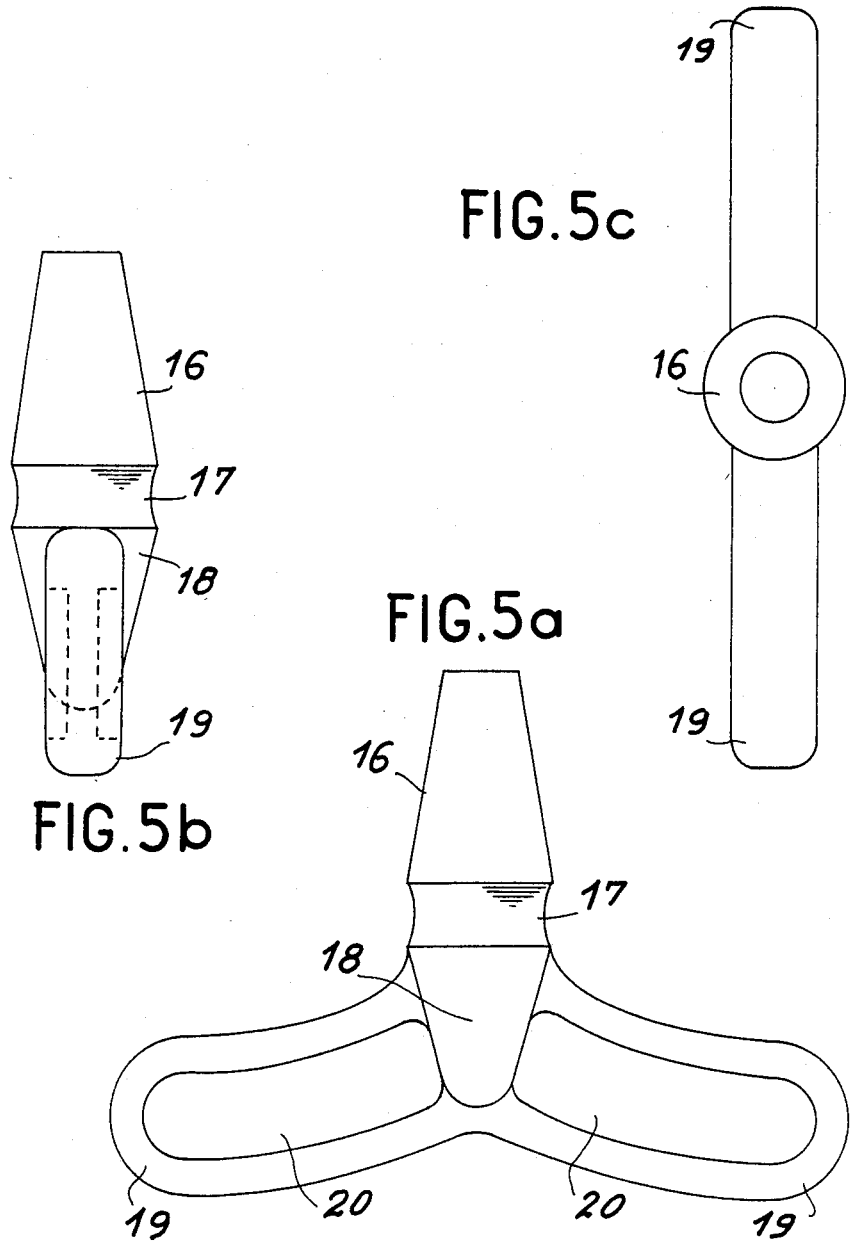

DENTAL IMPLANTS AND ACCESSORIES THEREFOR

This is a continuation of application Ser. No. 416,675, filed Sept. 20, 1982 and now abandoned. FIELD OF THE INVENTION The present invention relates to a novel technique for implanting teeth, and more particularly dental implants in the jawbone of a patient.

The object of the invention is to employ new carbon carbon composite materials for making dental implants easier to insert and providing best post-surgical results.

The biological and biomechanical qualities, namely, the compatibility with living tissues, of carbon carbon composite materials make them particularly suitable for making dental prosthesis as has already been proposed.

SUMMARY OF THE INVENTION

A main object of the present invention is to provide a complete dental procedure for installing implants of carbon carbon composite materials.

According to the invention there is provided a dental implant comprising a one-piece structure of carbon carbon composite material having a texture of carbon fibers and a fiber inter connecting matrix also of carbon, the one-piece structure comprising a root portion adapted to protrude into the jawbone and comes into direct contact with bone tissue and a coronal portion adapted to emerge from the gum and receive a dental crown or prosthesis. Such a dental crown or prosthesis may be received directly or indirectly on the coronal portion of the one-piece unit.

Different types of implants have been made from such a one-piece structure which will now be described by way of example as well as other accessories for the securement of various dental crowns or prosthesis and designed to be adapted to the novel implants according to the invention. This includes accessories for installing the implants and particularly for facilitating implantation with a minimum of constraints for the patient and better conditions of securement precision and reduced post-surgical results.

The description will be made with reference to the accompanying drawings of various embodiments of implants and accessories.

BRIEF DESCRIPTION OF THE DRAWINGS

FIGS. 5a, 5b and 5c show two elevational and a plan view respectively of a finned implant;

FIG. 1a shows a first embodiment of the implant comprising a cylindrical root portion 1 extended at its upper end by a frustoconical coronal portion 2 for securing a dental crown or prosthesis. The implant is one-piece structure of a carbon carbon composite material comprised of a carbon fiber texture and a fiber interconnecting matrix also made of carbon. The material used comprises more than 99% pure carbon, its specific gravity is about 1.7 and its module of elasticity-its most important property-is 4,000 kg/mm² whereas that of the jawbone is 1,500 kg/mm². Carbon carbon composites have biological and biomechanical properties, in particular compatibility with living tissues, which make them especially suitable for constructing dental implants.

Figure 1A:
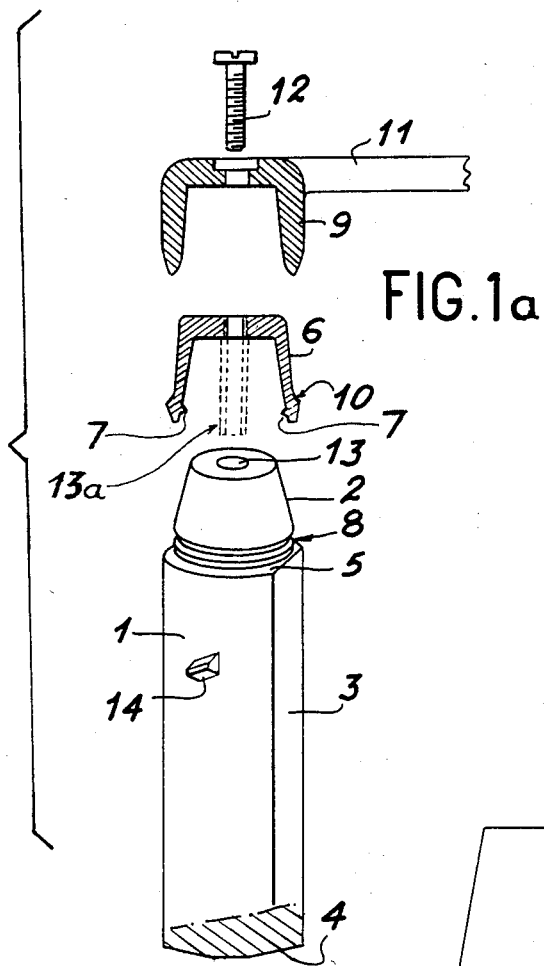
FIG. 1a shows a first cylindrical implant embodiment and various supplementary components for mounting a crown thereon.

The cylindrical root portion 1 is solid, its diameter is 3.5 mm but may of course vary, and is equal to the length of the cylindrical root portion. The cylindrical root portion 1 has a flat 3 parallel to the axis of the cylindrical root portion with a width of 1.5 mm, in the illustrated embodiment. the base 4 of the cylindrical root portion 1 is frustoconical with blunted edges. The flat 3 prevents the piston effect during insertion of the implant into the bone socket and favors postsurgical exsudation. Ultimately it prevents rotation of the implant. The cylindrical root portion 1 may have two or more such flats parallel to the axis of the cylinder of the same or different widths.

The surface of the implant is directly in contact with the jawbone, the connective tissue acting as a connection with the bone tissue and thereby partaking in the securement of the implant.

The upper frustoconical coronal portion 2 is separated from the cylindrical root portion 1 by a shoulder 5 which acts as an abutment for a frustoconical protective sleeve or socket 6. The sleeve 6 is detented on the coronal portion 2 of the implant by means of a circular internal rib 7 cooperating with a complementary groove 8 formed at the base of the frustoconical coronal portion 2.

The sleeve 6 is covered by a cap 9 comprising a body of revolution having a lower edge abutting against an external shoulder 10 formed at the base of the sleeve 6. The cap 9 is connected to another identical cap (not shown) by the medium of a connecting bar 11. The sleeve 6, the cap 9 and the bar 11 are all made of a noble metal alloys.

The bar 11 is removably mounted by means of a screw 12 traversing the cap 9 and screwed into the sleeve 6, the end of the screw 12 being received in a smooth blind hole 13 provided along the axis of the implant. Alternatively, the hole 13 may accommodate a metal liner or insert, illustrated in dotted lines at 13a. The liner or insert 13a is fixed to the sleeve 6 and internally threaded for threaded engagement with screw 12.

The assembly of components 1, 2, 6 and 9 without bar 11 may of course accommodate a dental crown or prosthesis directly. Accessories for installing such crowns or prosthesis on the connecting bar 11 will be described below in conjunction with FIG. 9–11.

FIG. 1a also shows, according to a modified embodiment, a keying lug 14 projecting from the cylindrical surface of the cylindrical portion 1 of the implant. The lug 14 comprises a thread segment of triangular section about 3 mm long and 2 mm height. The lug 14 is provided in the upper third of the cylindrical root portion 1 and is adapted to be engaged in an suitably shaped female thread in the wall of the bone socket for receiving the implant to fix its position in a precise and secure manner therein.

FIGS. 1b–1e illustrate alternative embodiments of implants having a cylindrical root portion with a flat.

Figure 1B:
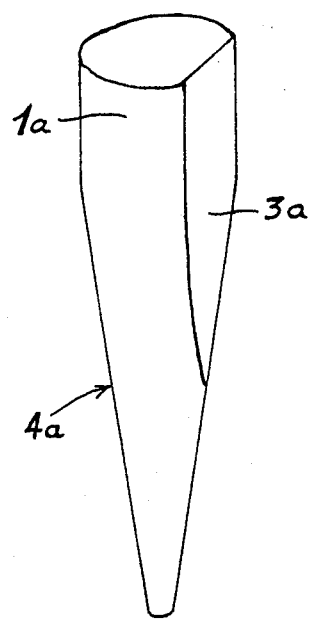
FIGS. 1b–1e *illustrate various alternative implant embodiments;*

FIG. 1b shows the root portion 1a of an implant comprising a cylindrical portion with a flat 3a and a frustoconical portion 4a having an angle (about 20°) very must smaller that the angle (120°) of the frustoconical portion 4 of the implant in FIG. 1a. In both embodiments the lower tip of the frustoconical portion has a diameter of the order to 1.5 mm.

Figure 1C:
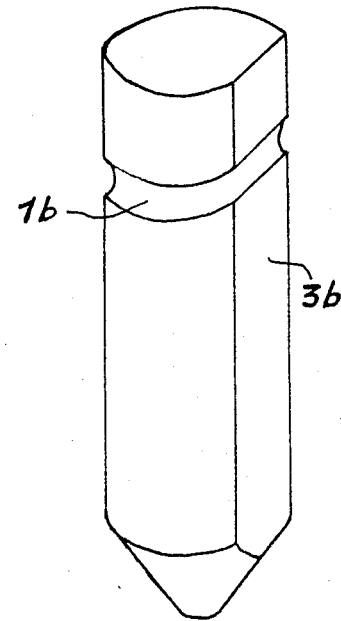
Figure 1D:
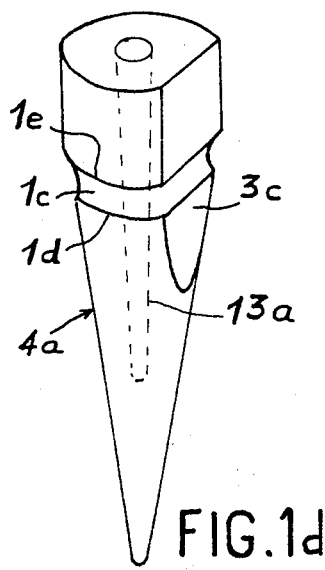

FIGS. 1c and 1d both show an embodiment of an implant having a cylindrical portion, a flat 3b, 3c and a groove 1b, 1c of rounded section disposed between the cylindrical coronal portion and the root portion. The groove 1b, 1c is intended to permit the gum to grip the implant and act as a hermetic seal. The groove 1b, 1c is formed in a zone of the implant having a diameter of about 10mm and the distance between the edges of the grooves, i.e., its height, is of the order of 2.5 mm.

In the FIG. 1d embodiment the frustoconical portion 4a extends slightly above the groove 1c and therefore the lower edge 1d of the groove 1c is set back from the upper edge 1e of the groove 1c, the surface of the groove runs gradually into the frustoconical portion 4a.

As shown in FIG. 1d, which may be the case with the embodiment of FIG. 1b, the implant may comprises a coaxial central blind bore 13a which tapers in the direction of the lower tip of the frustoconical root portion 4a.

Figure 1E:
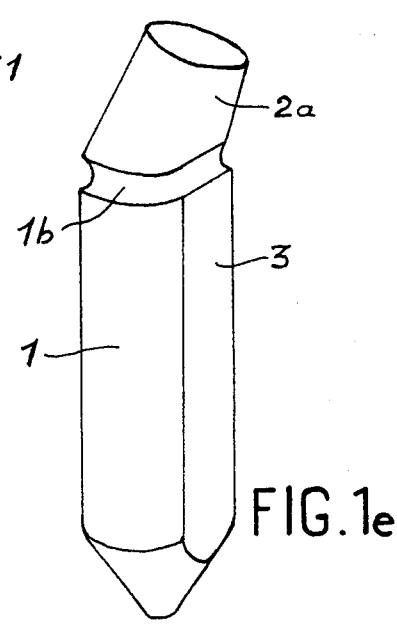

FIG. 1e shows an implant comprising a cylindrical root portion 1 having a flat 3 and a groove 1b and a cylindrical coronal portion or post 2a having a circular cross section, the axis of the cylindrical coronal portion 2a being at inclined relative to the axis of the cylindrical root portion 1.

Figure 2:
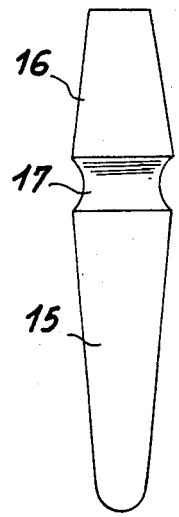
FIG. 2 shows another implant embodiment with frustoconical root and coronal portions.

FIG. 2 shows another embodiment of the implant according to the invention in which the root portion 15 is frustoconical and tapers downwards (into the bone tissue) and has a round lower end. The frustoconical coronal portion 16 is separated from the frustoconical root portion 15 by a circular groove 17 having a rounded cross section intended to permit gum growth into the groove to grip the implant and act as a hermetic seal. The respective shapes and dimensions of the coronal portion 16, the groove 17 and the root portion 15 may of course vary depending on the particular application.

Figure 3A:
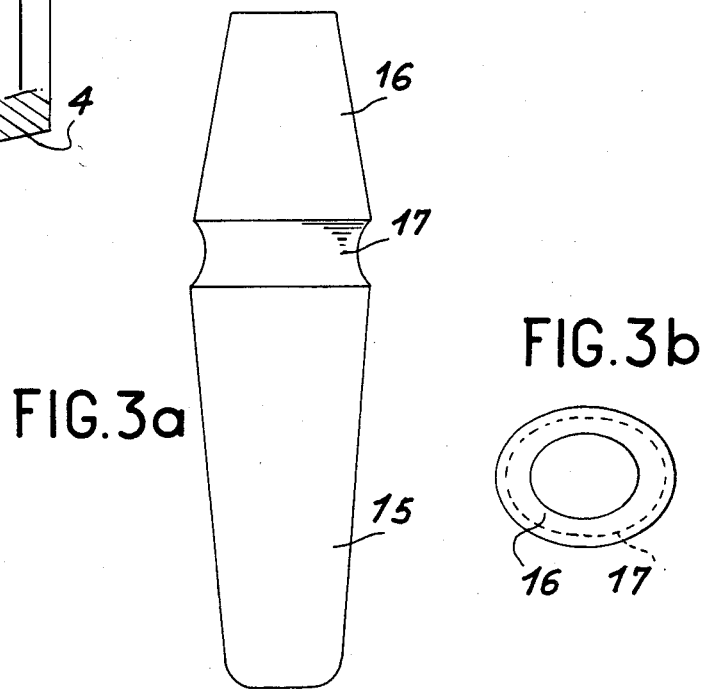
FIGS. 3a and 3b are, respectively, an elevational view and a top plan view of a modified embodiment of the implant of FIG. 2, FIGS. 4a and 4b show two elevational views of another modified embodiment of the implant of FIG. 2.
Figure 3B:
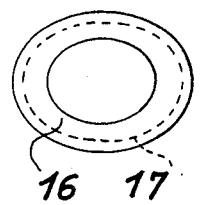

FIGS. 3a and 3b illustrate another embodiment, similar to the embodiment of FIG. 2, in which the coronal portion 16, the groove 17 and the root portion 15 are all of elliptical rather than circular section.

Figure 4A:
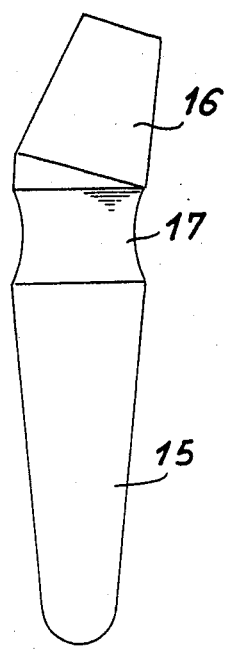
Figure 4B:
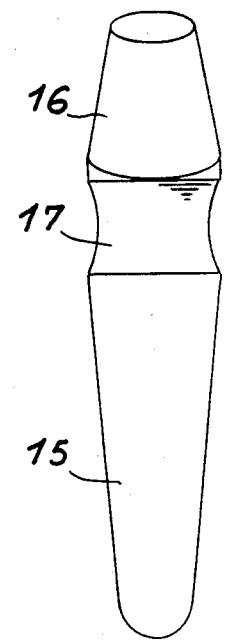

FIGS. 4a and 4b illustrate another modified embodiment of an implant having a frustoconical root portion 15, a frustoconical coronal portion 16 and a peripheral groove 17 therebetween.

In FIGS. 4a and 4b embodiment, the axis of the coronal portion 16 is at an angle to the axis of the root portion 15 and a connecting zone of suitable configuration connects the coronal portion 16 to the peripheral groove 17.

FIGS. 5a, 5b and 5c illustrate another type of implant in conformity with the invention. It is a finned or blade implant of one-piece construction made of the same composite material as the preceding embodiments. The coronal portion 16 and the circular peripheral groove 17 are similar to those of the embodiments of FIGS. 2, 3a and 3b, and 4a and 4b.

The root portion 18 also is frustoconical but it is extended by a two symmetrical fins of blades 19 of constant thickness lying in an axial plane and connected to each other beyond and in alignment with the tip of the frustoconical root portion 18. The central parts of blades or fins 19 are hollowed out at 20 to facilitate securement by bone tissue. The size and shape of the fins 19 may vary to a great extent. Finally, the finned or blade implant of FIGS. 5a–5c comprises a single coronal portion or post 16 for receiving a dental crown or prosthesis.

Figure 6B:
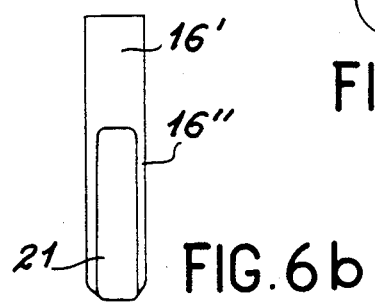
FIGS. 6a and 6b shows a perspective view and an end elevational view of another kind of finned implant.
Figure 6A:
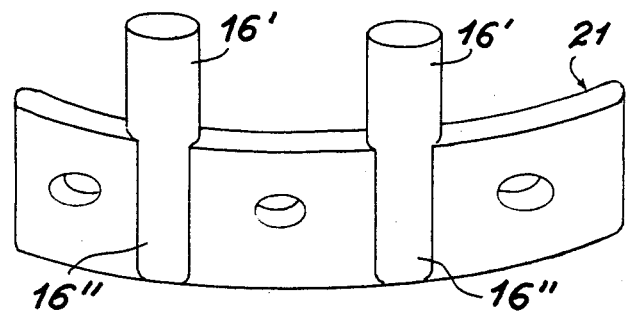

FIGS. 6a and 6b show a finned or blade implant with two identical cylindrical coronal portions or posts 16' fixed to a thin curved plate like blade 21 of constant thickness slightly less than the diameter of the coronal portions 16'. The blade 21 is planar but can be concave to mate with the anatomical shape of the jawbone and, in addition, perforated to permit the formation of bridges of bone tissue therethrough. The posts or coronal portions 16' are extended by root portions 16" which are in line with the blade 21 and their lower ends are chamfered as in the case of the embodiment of FIG. 1a.

Figure 7:
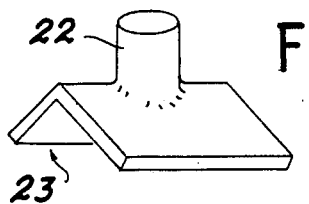
FIG. 7 shows a perspective view of a juxta-bone implant with a gable roof-shaped saddle.

FIG. 7 shows another embodiment of the implant according to the invention of the juxta-bone type. This implant comprises a cylindrical post or coronal portion 22 and a gable roof-shaped saddle or root portion 23. The root portion 23 comprises two planar plates forming a dihedral angle which is variable as a function of the jawbone configuration. Depending on the dimensions, the root portion 23 may support one or two posts or coronal portions 22 which straddle the ridge of the roof-shaped root portion 23.

Figure 8:
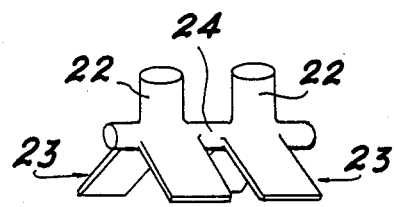
FIG. 8 shows a perspective view of a modified embodiment of the implant of FIG. 7.

The FIG. 8 embodiment shows twin implants, i.e., two implants of the type shown in FIG. 7, interconnected by a transverse cylindrical rod 24, the implants being at the same level.

All the foregoing described and illustrated embodiments have in common, in accordance with the invention, the fact that their root and coronal portions are part of a one-piece structure of carbon carbon composite material, the root portion material coming into direct contact with the bone tissue.

Figure 9:
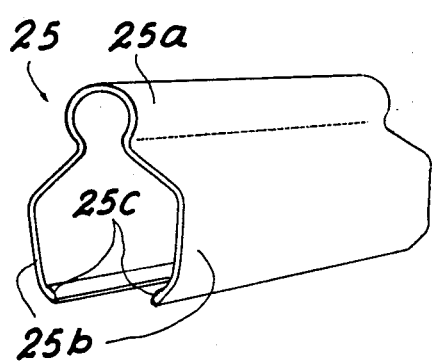
FIG. 9 shows a perspective view of a clip for mounting a crown.
Figure 10:
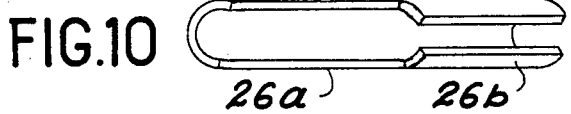
FIG. 10 shows a perspective view of a sheath adapted to be received on the crown fitting.
Figure 11:
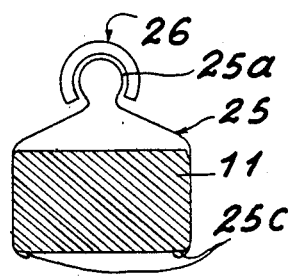
FIG. 11 shows a cross sectional view of the clip on a connecting bar with the clip and sheath of FIGS. 9 and 10.

FIGS. 9–11 show accessories for installing and mounting the dental crown or prosthesis on a connecting bar of the type illustrated in FIG. 1a. The bar 11 is of generally rectangular cross section having a face turned toward the jawbone which may be convex or concave for prophylactic reasons.

One or more clips or fittings 25 (FIG. 9) of noble metal alloys are fitted or clipped on the bar 11 and a polytetrafluorethylene sheath 26 (FIG. 10) is slid on the clips or fittings for supporting the actual crown or prosthesis. Each clip or fitting 25 comprises a cylindrical portion 25a for receiving the sheath 26 and two symmetrical legs 25b for clipping the clip or fitting 25 to the bar 11. Beads 25c are provided at the free ends of the legs 25b to assist the holding action of the clip or fitting 25.

The sheath 26 comprises a semicylindrical portion 26a for positioning and sliding on the cylindrical portion 25a of the clip or fitting 25 and a three-quarter cylindrical portion 26b for locking the sheath 26 on the clip or fitting 25. FIG. 11 illustrates the assembly of the various components on the connecting bar 11. It should be noted that the sheath 26, and therefore the crown or prosthesis (not shown), may be angularly adjusted by rotation on the sheath 26 about the axis of the cylindrical portion 25a of the clip or fitting 25. This pivotal mounting permits an adaptation of the angle of inclination of the crown or prosthesis on the coronal crest.

Since various implants according to the invention are inserted directly into the bone tissue it is necessary that the bone tissue be drilled with precision both with regard to the position in the jawbone and the dimensions. It is also of import to provide impeccable surface conditions. Further, to ensure optimal installation conditions for implants, a special dental surgical instrument or punch has been developed as shown in FIGS. 12a and 12b.

The surgical instrument which is intended for cutting the gums prior to drilling in the bone tissue comprises a tool steel tube 27 having a knurled knob 28 at the upper end thereof. The tube 27 is split at 29. One of the edges 29a of the slit lies along a generatrix of the cylinder and defines a cutting edge whereas the other edge 29b is bent inwardly toward the axis as shown in end view of FIG. 12b. The free end 29c of the bent portion is also a cutting edge. Such an arrangement permits precision cutting and careful incision of the mucous membrane as the surgical instrument is rotated, the edge 29c scraping clean the part of the bone tissue which is subsequently to be drilled.

Figure 12C:
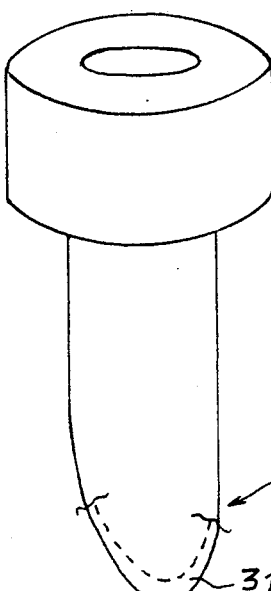
FIG. 12c shows an alternative embodiment of the socketforming surgical instrument of FIGS. 12a and 12b.
Figure 12A:
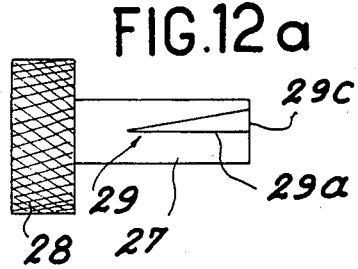
FIGS. 12a and 12b show a side view and an end view, respectively, of a dental surgical instrument for forming a socket for receiving implants according to the invention.
Figure 12B:

FIG. 12c illustrates an alternative embodiment of the surgical instrument having a cutting portion 30 which is generally of the shape of a woman's finger nail which has an inward bevel 31.

Finally, the invention is not intended to be limited to the various illustrated and described embodiments but on the contrary is intended to cover all variations and alternatives understood to those skilled in the art without departing from the spirit and scope of the invention.

What is claimed is:

1. A dental implant comprising a one-piece structure of carbon carbon composite material having a structure of carbon fibers and a fiber interconnecting matrix also of carbon, said one-piece structure comprising a cylindrical root portion having a cylindrical surface adapted to extend into a cylindrical recess in a jawbone and to come into direct contact with bone tissue and a frusto-conical coronal portion adapted to project from a gum and receive a dental crown, said root portion having at least one flat formed in said cylindrical surface and extending parallel to the axis of said root portion.

2. The implant of claim 1, wherein said at least one flat is of constant width and extends along the entire length of said cylindrical root portion.

3. The implant of claim 2, wherein the lower end of said cylindrical root portion is slightly frustoconical with blunted edges, the angle of said frustoconical lower end ranging between about 20° and 120°.

4. The implant of claim 2, wherein said cylindrical root portion comprises a lug having a thread segment adapted to be keyed into a suitably configured wall in a cylindrical socket in the jawbone.

5. The implant of claim 1, wherein a circular peripheral groove of rounded cross section is provided in said one-piece structure between said root portion and said coronal portion, said root and coronal portions both being substantially bodies of revolution.

6. The implant of claim 5, wherein the axis of said coronal portion is inclined relative to the axis of said root portion.

* * * * *